(12) United States Patent
Kuwahara et al.

(10) Patent No.: US 9,233,909 B2
(45) Date of Patent: Jan. 12, 2016

(54) PRODUCTION METHOD FOR AMINO COMPOUND

(75) Inventors: Hisayuki Kuwahara, Kanagawa (JP); Tomotaka Wada, Kanagawa (JP)

(73) Assignee: MITSUBISHI GAS CHEMICAL COMPANY, INC., Tokyo (JP)

( * ) Notice: Subject to any disclaimer, the term of this patent is extended or adjusted under 35 U.S.C. 154(b) by 8 days.

(21) Appl. No.: 13/981,008

(22) PCT Filed: Jan. 16, 2012

(86) PCT No.: PCT/JP2012/050704
§ 371 (c)(1),
(2), (4) Date: Jul. 22, 2013

(87) PCT Pub. No.: WO2012/105303
PCT Pub. Date: Aug. 9, 2012

(65) Prior Publication Data
US 2013/0303805 A1    Nov. 14, 2013

(30) Foreign Application Priority Data

Feb. 1, 2011    (JP) .................. 2011-019995

(51) Int. Cl.
*C07C 211/00* (2006.01)
*C07C 209/60* (2006.01)
*C07C 213/00* (2006.01)
*C07C 213/04* (2006.01)
*C07C 213/02* (2006.01)

(52) U.S. Cl.
CPC ............. *C07C 209/60* (2013.01); *C07C 213/00* (2013.01); *C07C 213/02* (2013.01); *C07C 213/04* (2013.01); *C07C 2101/14* (2013.01); *C07C 2102/42* (2013.01)

(58) Field of Classification Search
None
See application file for complete search history.

(56) References Cited

U.S. PATENT DOCUMENTS

| 7,057,075 | B2 * | 6/2006 | Bohling et al. ............... 564/485 |
| 7,157,606 | B2 * | 1/2007 | Echigo et al. ................. 564/485 |
| 7,364,668 | B2 * | 4/2008 | Kuwahara et al. ........ 252/182.13 |
| 2002/0055605 | A1 | 5/2002 | Yonehama et al. |
| 2004/0254399 | A1 | 12/2004 | Boehling et al. |

FOREIGN PATENT DOCUMENTS

| CN | 1649825 A | 8/2005 | |
| EP | 1 188 740 A2 | 3/2002 | |
| JP | 2002-161076 | 6/2002 | |
| JP | 2011088863 | * 5/2011 | ............ C07C 209/60 |
| WO | WO 02/00597 A2 | 1/2002 | |

OTHER PUBLICATIONS

Combined Chinese Office Action and Search Report issued Jul. 17, 2014 in Patent Application No. 201280006082.X (with English translation of categories of cited documents).
International Search Report issued Apr. 17, 2012 in PCT/JP2012/050704.
New Experimental Chemistry Lecture vol. 8, Synthesis of Inorganic Compounds(I), edited by The Chemical Society of Japan Maruzen Co., Ltd., 1976, 2 pages.

* cited by examiner

*Primary Examiner* — Clinton Brooks
(74) *Attorney, Agent, or Firm* — Oblon, McClelland, Maier & Neustadt, L.L.P.

(57) ABSTRACT

The present invention relates to a process for producing an amino compound by subjecting a polyamine and an alkenyl compound to addition reaction in the presence of an alkali metal hydride compound which is capable of supplying the amino compound in a stable manner without occurrence of odor.

14 Claims, No Drawings

PRODUCTION METHOD FOR AMINO COMPOUND

CROSS REFERENCE TO RELATED APPLICATIONS

The present application is a 35 U.S.C. §371 national stage patent application of international patent application PCT/JP2012/050704, filed on Jan.16, 2012, published as WO 2012/105303 on Aug. 9, 2012, the text of which is incorporated by reference, and claims the benefit of the filing date of Japanese Patent Application No. 2011-019995, filed on Feb. 1, 2011, the text of which is also incorporated by reference.

TECHNICAL FIELD

The present invention relates to a process for producing an amino compound by subjecting a polyamine and an alkenyl compound to addition reaction, and more particularly, to a process for producing an amino compound which is capable of supplying the amino compound in a stable manner without occurrence of odor.

BACKGROUND ART

An amino compound obtained by subjecting a polyamine and an alkenyl compound to addition reaction has a relatively small content of unreacted polyamine and exhibits a low viscosity. For this reason, an epoxy resin composition including an epoxy resin curing agent containing such an amino compound is capable of providing a cured product having good properties.

The amino compound may be produced by a known method in which a polyamine and an alkenyl compound are subjected to addition reaction (refer to Patent Document 1). In the production method, as a catalyst, there is used an alkali metal, an alkali metal amide or an alkylated alkali metal.

However, among these catalysts used upon producing the amino compound by addition reaction between the polyamine and the alkenyl compound, for example, sodium as the alkali metal has an extremely high reactivity and therefore tends to undergo abrupt reaction with even a trace amount of water in air. For this reason, care must be taken upon handing the catalysts containing sodium. On the other hand, lithium has a relatively moderate reactivity with water as compared to sodium but exhibits a reactivity with nitrogen, when handled in atmospheric air. Therefore, it is required to handle the catalysts containing lithium in an argon gas or a helium gas (refer to Non-Patent Document 1).

Also, in the case of using a catalyst containing lithium amide as the alkali metal amide, although the catalyst can be relatively readily handled in air, an ammonia gas tends to be generated when the catalyst is converted into a readily removable salt or hydroxide after termination of the reaction. The ammonia gas generated has an odor and therefore has posed the problem that any facility is required to prevent occurrence of the odor.

PRIOR ART DOCUMENTS

Patent Document

Patent Document 1; JP 2002-161076A

Non-Patent Document

Non-Patent Document 1; "New Experimental Chemistry Lecture Vol. 8; Synthesis of Inorganic Compounds (I)" edited by The Chemical Society of Japan, Maruzen Co., Ltd., 1976

SUMMARY OF THE INVENTION

Problem to be Solved by the Invention

An object of the present invention is to provide a process for producing an amino compound by subjecting a polyamine and an alkenyl compound to addition reaction which is capable of supplying the amino compound in a stable manner without occurrence of odor.

Means for Solving the Problem

As a result of extensive and intensive researches for solving the above conventional problems, the inventors have found that upon production of an amino compound by subjecting a polyamine and an alkenyl compound to addition reaction, when the addition reaction between the polyamine and the alkenyl compound is conducted in the presence of an alkali metal hydride compound, it is possible to produce the amino compound in an efficient manner. The present invention has been accomplished on the basis of the above finding That is, the present invention relates to a process for producing an amino compound by subjecting a polyamine and an alkenyl compound to addition reaction in which the addition reaction between the polyamine and the alkenyl compound is conducted in the presence of an alkali metal hydride compound.

Effect of the Invention

According to the present invention, in a process for producing an amino compound by subjecting a polyamine and an alkenyl compound to addition reaction, when the addition reaction between the polyamine and the alkenyl compound is conducted in the presence of an alkali metal hydride compound, it is possible to produce the amino compound as an aimed product in a stable manner without occurrence of odor.

PREFERRED EMBODIMENTS FOR CARRYING OUT THE INVENTION

The polyamine used in the present invention includes, for example, a polyamine represented by the following formula (1), a polyamine represented by the following formula (2), a cyclic aliphatic polyamine containing 9 or more carbon atoms and 2 or more amino groups in a molecule thereof as well as 3 or more active hydrogen atoms derived from the amino groups, a polyoxyalkylene polyamine or the like.

$$H_2N-CH_2-A-CH_2-NH_2 \quad (1)$$

wherein A is a phenylene group or a cyclohexylene group which may have a substituent group. Examples of the substituent group include an alkyl group having 1 to 3 carbon atoms, a halogen atom, and the like.

$$H_2N-(CH_2CH_2NH)_n-H \quad (2)$$

wherein n is an integer of 1 to 5.

Examples of the polyamine represented by the formula (1) which may be used in the present invention include o-xylylenediamine, m-xylylenediamine, p-xylylenediamine, 1,2-bis(aminomethyl)cyclohexane, 1,3-bis(aminomethyl)cyclohexane and 1,4-bis(aminomethyl)cyclohexane. Among these polyamines, preferred are m-xylylenediamine and 1,3-bis (aminomethyl)cyclohexane.

Examples of the polyamine represented by the formula (2) which may be used in the present invention include ethylenediamine, diethylenetriamine, triethylenetetramine, tetraethylenepentamine and pentaethylenehexamine. Among these polyamines, preferred are diethylenetriamine and Triethylenetetramine. In the formula (2), n is preferably an integer of 2 or 3.

Examples of the cyclic aliphatic polyamine containing 9 or more carbon atoms and 2 or more amino groups in a molecule thereof as well as 3 or more active hydrogen atoms derived from the amino groups which may be used in the present invention include menthenediamine, isophoronediamine, diaminodicyclohexyl methane, bis(4-amino-3-methylcydohexyl)methane, N-aminomethyl piperazine and norbornanediamine. Among these cyclic aliphatic polyamines, preferred are isophoronediamine and norbornanediamine.

Examples of the polyoxyalkylene polyamine which may be used in the present invention include polyoxyalkylene diamines such as polyoxyethylene diamine, polyoxypropylene diamine, polyoxytetramethylene diamine and poly(oxyethylene-oxypropylene)diamine; and polyoxyethylene triamine and polyoxypropylene triamine. Among these polyoxyalkylene polyamines, preferred are polyoxyethylene diamine, polyoxypropylene diamine and polyoxypropylene triamine.

The alkenyl compound used in the present invention is not particularly limited, and is preferably those alkenyl compounds having 2 to 10 carbon atoms. Examples of the alkenyl compounds having 2 to 10 carbon atoms include ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene and divinyl benzene.

In addition, the alkenyl compound is preferably an aromatic alkenyl compound. Examples of the aromatic alkenyl compound include styrene and divinyl benzene.

In the present invention, the amino compound can be obtained by subjecting the polyamine and the alkylene compound to addition reaction in the presence of an alkali metal hydride compound.

Upon synthesizing the amino compound according to the present invention, the alkali metal hydride compound is used as a catalyst.

Examples of the alkali metal hydride compound include lithium hydride, sodium hydride and potassium hydride. Among these alkali metal hydride compounds, lithium hydride is more suitably used.

In the present invention, the alkali metal hydride compound may be used in the form of a mixture with other substances having a catalytic activity. Examples of the other substances having a catalytic activity include an alkali metal, an alkali metal amide and an alkylated alkali metal.

Examples of the alkali metal include metallic lithium, metallic sodium and metallic potassium. Examples of the alkali metal amide include lithium amide, lithium diisopropyl amide and sodium amide. Examples of the alkylated alkali metal include methyl lithium and butyl lithium.

In the present invention, the above addition reaction between the polyamine and the alkenyl compound is preferably carried out in such a manner that after the alkali metal hydride compound is previously mixed and contacted with the polyamine, the resulting mixture is subjected to addition reaction with the alkenyl compound. With such a reaction procedure, active hydrogen atoms contained in the polyamine is enhanced in reactivity, so that the addition reaction of the polyamine with the alkenyl compound is allowed to proceed smoothly.

In the reaction between the alkali metal hydride compound and the polyamine, the alkali metal hydride compound is usually used in an amount of from 0.01 to 3% by mass, preferably from 0.02 to 2% by mass and more preferably from 0.03 to 1.0% by mass on the basis of a total amount of the alkali metal hydride compound and the polyamine. When the amount of the alkali metal hydride compound used is 0.01% by mass or more, the rate of the addition reaction between the polyamine and the alkenyl compound is good. When the amount of the alkali metal hydride compound used is 3% by mass or less, the reaction can be advantageously conducted from the economical viewpoints.

The reaction between the alkali metal hydride compound and the polyamine is usually conducted at a temperature of from 10 to 140° C. and preferably from 50 to 120° C. When the reaction temperature is 10° C. or higher, the alkali metal hydride compound and the polyamine can be efficiently reacted with each other. When the reaction temperature is 140° C. or lower, the reaction can be advantageously conducted from the economical viewpoints.

The time of the reaction between the alkali metal hydride compound and the polyamine is usually from 20 to 360 min and preferably from 30 to 60 min. When the reaction time is 20 min or longer, it is possible to sufficiently conduct the reaction between the alkali metal hydride compound and the polyamine. When the reaction time is 360 min or shorter, the reaction can be advantageously conducted from the economical viewpoints.

After completion of the reaction between the alkali metal hydride compound and the polyamine, the addition reaction of the polyamine with the alkenyl compound is usually carried out at a temperature of from 50 to 150° C. and preferably from 80 to 100° C. When the addition reaction temperature is 50° C. or higher, the rate of the addition reaction between the polyamine and the alkenyl compound is good. On the contrary, when the addition reaction temperature is 150° C. or lower, production of polymers of the alkenyl compound as by-products can be prevented.

It is preferred that after reacting the alkali metal hydride compound with the polyamine, the alkenyl compound is intermittently added in divided parts and subjected to addition reaction with the polyamine. When the alkali metal hydride compound, the polyamine and the alkenyl compound are subjected to the addition reaction while intermittently adding the alkenyl compound in divided parts, it is possible to suppress by-production of the polymers of the alkenyl compound. The number of the divided parts of the alkenyl compound to be intermittently added is not particularly limited, unless the polymers of the alkenyl compound are by-produced. The method of intermittently adding the alkenyl compound in divided parts and subjecting the alkenyl compound to the addition reaction may be an ordinary method. For example, there may be used a method of intermittently adding dropwise the alkenyl compound in divided parts through a dropping funnel to subject the alkenyl compound to the addition reaction, a method of intermittently adding the alkenyl compound in divided parts using a feed pump to subject the alkenyl compound to the addition reaction, or the like.

The reaction ratio of the alkenyl compound to the polyamine in the above reaction may be optionally determined according to properties and performance of the amino compound as the aimed product. For example, in the case where the obtained amino compound is used for curing an epoxy resin, the low reaction ratio of the alkenyl compound to the polyamine tends to have an adverse influence on properties of a cured product of the epoxy resin owing to a large amount of polyamine remaining unreacted. On the other hand, the high reaction ratio of the alkenyl compound to the polyamine tends to cause reduction in amount of active hydrogen atoms capable of reacting with the epoxy resin in the obtained amino compound.

When the alkenyl compound has one carbon-carbon double bond to be subjected to the addition reaction, the reaction ratio of the alkenyl compound per 1 mol of the polyamine is usually from 0.1 to 4.0 mol and preferably from 0.5 to 2.0 mol.

The reaction solution obtained after completion of the reaction contains the amino compound produced by the reaction and the alkali metal hydride compound. The alkali metal hydride compound can be removed by filtration to some extent. When subjecting the reaction solution to filtration, an acid such as hydrochloric acid, a hydrogen chloride gas and acetic acid, an alcohol such as methanol and ethanol, water, etc., may be added to the reaction solution before the filtration to convert the alkali metal hydride compound into a salt readily removable by the filtration. For example, when adding water to the reaction solution, the alkali metal hydride compound is converted into a hydroxide thereof which can be readily removed by the filtration.

After completion of the addition reaction with the alkenyl compound, the resulting reaction solution is held at the above reaction temperature for 30 to 120 min to thereby obtain an amino compound containing the unreacted alkenyl compound in an amount of 1% by mass or less and having stable properties.

EXAMPLES

The present invention will be described in more detail below by referring to the following examples. It should be noted, however, that the following examples are only illustrative and not intended to limit the invention thereto.

Meanwhile, the amino compound produced was analyzed by gas chromatography (hereinafter referred to merely as "GC analysis") under the following conditions.

Column: "Ultra Alloy-1" available from Frontier Laboratories Ltd. (length: 15 m; film thickness: 1.5 μm; inner diameter: 0.5 mm)

Column temperature: 110° C./10 min+heating at 10° C./min+300° C./60 min

In addition, the amino compound thus produced was identified and confirmed by NMR analysis in the same manner as described in Patent Document 1 (JP 2002-161076A).

Example 1

A 2 L flask equipped with a stirrer, a thermometer, a nitrogen inlet tube, a dropping funnel and a cooling tube was rapidly charged with 817.2 g (6.0 mol) of m-xylylenediamine ("MXDA" available from Mitsubishi Gas Chemical Co., Inc.; molecular weight: 136.2) and 1.0 g (0.13 mol) of lithium hydride (reagent available from Merck AG), and the contents of the flask were heated to 80° C. in a nitrogen flow while stirring. Thereafter, the resulting reaction mixture was stirred at 80° C. for 30 min, and 625. 2 g (6.0 mol) of styrene (guaranteed reagent available from Wako Pure Chemical Industries, Ltd.) were added dropwise thereto over 2 h while maintaining a temperature of the reaction mixture at 80° C. After completion of the dropwise addition, the resulting reaction solution was held at 80° C. for 30 min. Thereafter, 23.4 g (1.3 mol) of distilled water corresponding to a molar amount 10 times that of the lithium hydride charged were added dropwise to the reaction solution and then stirred. At this time, no odor was generated. After precipitates in the flask were removed by filtration, the resulting reaction solution was subjected to distillation under reduced pressure to remove water therefrom, thereby obtaining 1381.7 g of an amino compound A. The amount of styrene remaining unreacted was 0.1% by mass.

As a result of subjecting the thus obtained amino compound A to GC analysis, four peaks were observed in addition to the peak attributed to the unreacted MXDA. When the four peaks were expressed by a, b, c and d in the order to their retention times, the area ratios of the respective peaks including the peak of the unreacted MXDA were 15.2% for the peak of unreacted MXDA; 49.9% for the peak a; 3.1% for the peak b; 28.7% for the peak c; and 3.1% for the peak d.

Example 2

After allowing 817.2 g (6.0 mol) of MXDA and 1.0 g (0.13 mol) of lithium hydride (reagent available from Merck AG) to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 30 min, and 625. 2 g (6.0 mol) of styrene (guaranteed reagent available from Wako Pure Chemical Industries, Ltd.) were added dropwise thereto over 2 h while maintaining a temperature of the reaction mixture at 80° C. After completion of the dropwise addition, the resulting reaction solution was held at 80° C. for 30 min. Thereafter, 23.4 g (1.3 mol) of distilled water corresponding to a molar amount 10 times that of the lithium hydride charged were added dropwise to the reaction solution and then stirred. At this time, no odor was generated. After precipitates in the flask were removed by filtration, the resulting reaction solution was subjected to distillation under reduced pressure to remove water therefrom, thereby obtaining 1381.7 g of an amino compound B. The amount of styrene remaining unreacted was 0.3% by mass.

As a result of subjecting the thus obtained amino compound B to GC analysis, four peaks were observed in addition to the peak attributed to the unreacted MXDA. When the four peaks were expressed by a, b, c and d in the order to their retention times, the area ratios of the respective peaks including the peak of the unreacted MXDA were 15.4% for the peak of unreacted MXDA; 51.0% for the peak a; 3.0% for the peak b; 27.8% for the peak c; and 2.8% for the peak d.

Example 3

After allowing 681.0 g (5.0 mol) of MXDA and 1.1 g (0.14 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 30 min, and 651. 3 g (6.25 mol) of styrene were added dropwise thereto over 2.5 h while maintaining a temperature of the reaction mixture at 80° C. After completion of the dropwise addition, the resulting reaction solution was held at 80° C. for 30 min. Thereafter, 25.2 g (1.4 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 1271.2 g of an amino compound C. The amount of styrene remaining unreacted was 0.2% by mass.

As a result of subjecting the thus obtained amino compound C to GC analysis, four peaks were observed in addition to the peak attributed to the unreacted MXDA. When the four peaks were expressed by a, b, c and d in the order to their retention times, the area ratios of the respective peaks including the peak of the unreacted MXDA were 9.7% for the peak of unreacted MXDA; 45.3% for the peak a; 3.3% for the peak b; 34.8% for the peak c; and 6.9% for the peak d.

Example 4

After allowing 853.2 g (6.0 mol) of 1,3-bis(aminomethyl) cyclohexane ("1,3-BAC" available from Mitsubishi Gas Chemical Co., Inc.; molecular weight: 142.2) and 1.0 g (0.13 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 120 min, and 625. 2 g (6.0 mol) of styrene were added dropwise thereto over 2 h while maintaining a temperature of the reaction mixture at 80° C. After completion of the dropwise addition, the resulting reaction solution was held at 80° C. for 60 min. Thereafter, 23.4 g (1.3 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 1409.7 g of an amino compound D. The amount of styrene remaining unreacted was 0.3% by mass.

As a result of subjecting the thus obtained amino compound D to GC analysis, four peaks were observed in addition to the peak attributed to the unreacted 1,3-BAC. When the four peaks were expressed by a, b, c and d in the order to their retention times, the area ratios of the respective peaks including the peak of the unreacted 1,3-BAC were 15.1% for the peak of unreacted 1,3-BAC; 54.2% for the peak a; 0.7% for the peak b; 28.0% for the peak c; and 2.0% for the peak d.

Example 5

After allowing 711.0 g (5.0 mol) of 1,3-BAC and 1.2 g (0.15 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 120 min, and 651. 3 g (6.25 mol) of styrene were added dropwise thereto over 2.5 h while maintaining a temperature of the reaction mixture at 80° C. After completion of the dropwise addition, the resulting reaction solution was held at 80° C. for 60 min. Thereafter, 27.0 g (1.5 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 1307.1 g of an amino compound E. The amount of styrene remaining unreacted was 0.2% by mass.

As a result of subjecting the thus obtained amino compound E to GC analysis, four peaks were observed in addition to the peak attributed to the unreacted 1,3-BAC. When the four peaks were expressed by a, b, c and d in the order to their retention times, the area ratios of the respective peaks including the peak of the unreacted 1,3-BAC were 9.5% for the peak of unreacted 1,3-BAC; 49.4% for the peak a; 1.0% for the peak b; 35.2% for the peak c; and 4.9% for the peak d.

Example 6

After allowing 412.7 g (4.0 mol) of diethylenetriamine ("DETA" guaranteed reagent available from Kanto Kagaku Co., Ltd.) and 0.9 g (0.11 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 30 min, and 651. 3 g (6.25 mol) of styrene were added dropwise thereto over 2 h while maintaining a temperature of the reaction mixture at 80° C. After completion of the dropwise addition, the resulting reaction solution was held at 80° C. for 30 min. Thereafter, 19.8 g (1.1 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 777.1 g of an amino compound F. The amount of styrene remaining unreacted was 0.2% by mass.

As a result of subjecting the thus obtained amino compound F to GC analysis, three peaks were observed in addition to the peak attributed to the unreacted DETA. When the three peaks were expressed by a, b and c in the order to their retention times, the area ratios of the respective peaks including the peak of the unreacted DETA were 11.8% for the peak of unreacted DETA; 41.2% for the peak a; 38.5% for the peak b; and 8.5% for the peak c.

Example 7

After allowing 584.8 g (4.0 mol) of triethylenetetramine ("TETA" guaranteed reagent available from Kanto Kagaku Co., Ltd.) and 1.0 g (0.13 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 30 min, and 651. 3 g (6.25 mol) of styrene were added dropwise thereto over 2.5 h while maintaining a temperature of the reaction mixture at 80° C. After completion of the dropwise addition, the resulting reaction solution was held at 80° C. for 30 min. Thereafter, 23.4 g (1.3 mol) of distilled water corresponding to a molar amount 10 times that of the lithium hydride charged were added to the reaction solution and then stirred for 1 h. After precipitates in the flask were removed by filtration, the resulting reaction solution was subjected to distillation under reduced pressure to remove water therefrom, thereby obtaining 991.2 g of an amino compound G. The amount of styrene remaining unreacted was 0.4% by mass.

Example 8

After allowing 681.2 g (4.0 mol) of isophoronediamine ("IPDA" available from Degussa AG) and 1.1 g (0.14 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 120 min, and 416.8 g (4.0 mol) of styrene were added dropwise thereto over 2.5 h while maintaining a temperature of the reaction mixture at 80° C. After completion of the dropwise addition, the resulting reaction solution was held at 80° C. for 120 min. Thereafter, 25.2 g (1.4 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 1033.6 g of an amino compound H. The amount of styrene remaining unreacted was 0.7% by mass.

As a result of subjecting the thus obtained amino compound H to GC analysis, three peaks were observed in addition to the peak attributed to the unreacted IPDA. When the three peaks were expressed by a, b and c in the order to their retention times, the area ratios of the respective peaks including the peak of the unreacted IPDA were 11.0% for the peak of unreacted IPDA; 54.2% for the peak a; 9.0% for the peak b; and 25.8% for the peak c.

Example 9

After allowing 617.2 g (4.0 mol) of norbornanediamine ("NBDA" available from Mitsui Chemicals, Inc.) and 1.1 g (0.14 mol) of lithium hydride to stand in air under the conditions of 23° C. and 50% RH for 1 min, they were charged into a flask of the same type as used in Example 1, and the contents of the flask were heated to 80° C. in a nitrogen flow while stirring. Thereafter, the resulting reaction mixture was stirred at 80° C. for 120 min, and 416.8 g (4.0 mol) of styrene were added dropwise thereto over 2.5 h while maintaining a temperature of the reaction mixture at 80° C. After completion of the dropwise addition, the resulting reaction solution was held at 80° C. for 120 min. Thereafter, 25.2 g (1.4 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 971.2 g of an amino compound I. The amount of styrene remaining unreacted was 0.7% by mass.

Example 10

After allowing 460.0 g (2.0 mol) of polyoxypropylene diamine ("JEFFAMINE D-230" available from Huntsman Corp.; molecular weight: 230) and 8.0 g (1.0 mol) of lithium hydride to stand in air under the conditions of 23° C. and 50% RH for 1 min, they were charged into a flask of the same type as used in Example 1, and the contents of the flask were heated to 100° C. in a nitrogen flow while stirring. Thereafter, the resulting reaction mixture was stirred at 100° C. for 120 min, and 208.4 g (2.0 mol) of styrene were added dropwise thereto over 4 h while maintaining a temperature of the reaction mixture at 100° C. After completion of the dropwise addition, the resulting reaction solution was held at 100° C. for 120 min. Thereafter, 167.7 g (9.3 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 635.1 g of an amino compound J. The amount of styrene remaining unreacted was 0.9% by mass.

Example 11

After allowing 296.0 g (2.0 mol) of polyoxyethylene diamine ("JEFFAMINE EDR-148" available from Huntsman Corp.; molecular weight: 148) and 0.5 g (0.065 mol) of lithium hydride to stand in air under the conditions of 23° C. and 50% RH for 1 min, they were charged into a flask of the same type as used in Example 1, and the contents of the flask were heated to 100° C. in a nitrogen flow while stirring. Thereafter, the resulting reaction mixture was stirred at 100° C. for 30 min, and 208.4 g (2.0 mol) of styrene were added dropwise thereto over 2 h while maintaining a temperature of the reaction mixture at 100° C. After completion of the dropwise addition, the resulting reaction solution was held at 100° C. for 30 min. Thereafter, 11.7 g (0.65 mol) of distilled water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 479.1 g of an amino compound K. The amount of styrene remaining unreacted was 0.2% by mass.

Example 12

After allowing 806.0 g (2.0 mol) of polyoxypropylene triamine ("JEFFAMINE T-403" available from Huntsman Corp.; molecular weight: 403) and 11.9 g (1.5 mol) of lithium hydride to stand in air under the conditions of 23° C. and 50% RH for 1 min, they were charged into a flask of the same type as used in Example 1, and the contents of the flask were heated to 100° C. in a nitrogen flow while stirring. Thereafter, the resulting reaction mixture was stirred at 100° C. for 120 min, and 312.6 g (3.0 mol) of styrene were added dropwise thereto over 6 h while maintaining a temperature of the reaction mixture at 100° C. After completion of the dropwise addition, the resulting reaction solution was held at 100° C. for 120 min. Thereafter, 270.0 g (15.0 mol) of water corresponding to a molar amount 10 times that of the lithium hydride charged were added to the reaction solution and then stirred. After precipitates in the flask were removed by filtration, the resulting reaction solution was subjected to distillation under reduced pressure to remove water therefrom, thereby obtaining 1052.2 g of an amino compound L. The amount of styrene remaining unreacted was 0.9% by mass.

Comparative Example 1

A flask of the same type as used in Example 1 was rapidly charged with 817.2 g (6.0 mol) of MXDA and 2.9 g (0.13 mol) of lithium amide, and the contents of the flask were heated to 80° C. in a nitrogen flow while stirring. Then, 625.2 g (6.0 mol) of styrene were added dropwise to the flask over 2 h while maintaining a temperature of the reaction mixture at 80° C. After completion of the dropwise addition, the resulting reaction solution was held at 80° C. for 60 min. Thereafter, 23.4 g (1.3 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1379.6 g of an amino compound M. The amount of styrene remaining unreacted was 0.2% by mass.

Comparative Example 2

After allowing 817.2 g (6.0 mol) of MXDA and 2.9 g (0.13 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 625.2 g (6.0 mol) of styrene were added dropwise to the flask over 2 h while maintaining a temperature of the reaction mixture at 80° C. After completion of the dropwise addition, the resulting reaction solution was held at 80° C. for 60 min. Thereafter, 23.4 g (1.3 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1379.6 g of an amino compound N. The amount of styrene remaining unreacted was 2.5% by mass.

Comparative Example 3

After allowing 681.0 g (5.0 mol) of MXDA and 3.3 g (0.14 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 651.3 g (6.25 mol) of styrene were added dropwise to the flask over 2.5 h while maintaining a temperature of the reaction mixture at 80° C. After completion of the dropwise addition, the resulting reaction solution was held at 80° C. for 60 min. Thereafter, 25.2 g (1.4 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1270.9 g of an amino compound O. The amount of styrene remaining unreacted was 5.1% by mass.

Comparative Example 4

After allowing 853.2 g (6.0 mol) of 1,3-BAC and 3.0 g (0.13 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 625.2 g (6.0 mol) of styrene were added dropwise to the flask over 2 h while maintaining a temperature of the reaction mixture at 80° C. After completion of the dropwise addition, the resulting reaction solution was held at 80° C. for 120 min. Thereafter, 23.4 g (1.3 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1409.3 g of an amino compound P. The amount of styrene remaining unreacted was 5.2% by mass. When mixing 10 parts by mass of the amino compound P with 100 parts by mass of methanol, white precipitates were produced. Therefore, it was confirmed that polymers of styrene were by-produced.

Comparative Example 5

After allowing 711.0 g (5.0 mol) of 1,3-BAC and 3.4 g (0.15 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 651.3 g (6.25 mol) of styrene were added dropwise to the flask over 2.5 h while maintaining a temperature of the reaction mixture at 80° C. After completion of the dropwise addition, the resulting reaction solution was held at 80° C. for 120 min. Thereafter, 27.0 g (1.5 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1305.8 g of an amino compound Q. The amount of styrene remaining unreacted was 5.2% by mass. When mixing 10 parts by mass of the amino compound Q with 100 parts by mass of methanol, white precipitates were produced. Therefore, it was confirmed that polymers of styrene were by-produced.

Comparative Example 6

After allowing 412.7 g (4.0 mol) of DETA and 2.5 g (0.11 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 651.3 g (6.25 mol) of styrene were added dropwise to the flask over 2.5 h while maintaining a temperature of the reaction mixture at 80° C. After completion of the dropwise addition, the resulting reaction solution was held at 80° C. for 30 min. Thereafter, 19.8 g (1.1 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 777.0 g of an amino compound R. The amount of styrene remaining unreacted was 5.1% by mass.

Comparative Example 7

After allowing 584.8 g (4.0 mol) of TETA and 3.0 g (0.13 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 651.3 g (6.25 mol) of styrene were added dropwise to the flask over 2.5 h while maintaining a temperature of the reaction mixture at 80° C. After completion of the dropwise addition, the resulting reaction solution was held at 80° C. for 0.5 h. Thereafter, 23.4 g (1.3 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 990 g of an amino compound S. The amount of styrene remaining unreacted was 5.4% by mass.

Comparative Example 8

After allowing 681.2 g (4.0 mol) of IPDA and 3.3 g (0.14 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 416.8 g (4.0 mol) of styrene were added dropwise to the flask over 2.5 h while maintaining a temperature of the reaction mixture at 80° C. After completion of the dropwise addition, the resulting reaction solution was held at 80° C. for 120 min. Thereafter, 25.2 g (1.4 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1032.7 g of an amino compound T. The amount of styrene remaining unreacted was 10.8% by mass. When mixing 10 parts by mass of the amino compound T with 100 parts by mass of methanol, white precipitates were produced. Therefore, it was confirmed that polymers of styrene were by-produced.

Comparative Example 9

After allowing 617.2 g (4.0 mol) of NBDA and 3.3 g (0.14 mol) of lithium amide to stand in air under the conditions of 23° C. and 50% RH for 1 min, they were charged into a flask of the same type as used in Example 1, and the contents of the flask were heated to 80° C. in a nitrogen flow while stirring. Then, 416.8 g (4.0 mol) of styrene were added dropwise to the flask over 2.5 h while maintaining a temperature of the reaction mixture at 80° C. After completion of the dropwise addition, the resulting reaction solution was held at 80° C. for 120 min. Thereafter, 25.2 g (1.4 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 969.3 g of an amino compound U. The amount of styrene remaining unreacted was 10.9% by mass. When mixing 10 parts by mass of the amino compound U with 100 parts by mass of methanol, white precipitates were produced. Therefore, it was confirmed that polymers of styrene were by-produced.

Comparative Example 10

After allowing 460.0 g (2.0 mol) of "JEFFAMINE D-230" and 21.3 g (0.93 mol) of lithium amide to stand in air under the conditions of 23° C. and 50% RH for 1 min, they were charged into a flask of the same type as used in Example 1, and the contents of the flask were heated to 100° C. in a nitrogen flow while stirring. Then, 208.4 g (2.0 mol) of styrene were added dropwise to the flask over 4 h while maintaining a temperature of the reaction mixture at 100° C. After completion of the dropwise addition, the resulting reaction solution was held at 100° C. for 2 h. Thereafter, 167.7 g (9.3 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 635.0 g of an amino compound V. The amount of styrene remaining unreacted was 37.7% by mass. When mixing 10 parts by mass of the amino compound V with 100 parts by mass of methanol, white precipitates were produced. Therefore, it was confirmed that polymers of styrene were by-produced.

Comparative Example 11

After allowing 296.0 g (2.0 mol) of "JEFFAMINE EDR-148" and 1.5 g (0.065 mol) of lithium amide to stand in air under the conditions of 23° C. and 50% RH for 1 min, they were charged into a flask of the same type as used in Example 1, and the contents of the flask were heated to 100° C. in a nitrogen flow while stirring. Then, 208.4 g (2.0 mol) of styrene were added dropwise to the flask over 4 h while maintaining a temperature of the reaction mixture at 100° C. After completion of the dropwise addition, the resulting reaction solution was held at 100° C. for 30 min. Thereafter, 11.7 g (0.65 mol) of distilled water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 478.8 g of an amino compound W. The amount of styrene remaining unreacted was 5.9% by mass.

Comparative Example 12

After allowing 806.0 g (2.0 mol) of "JEFFAMINE T-403" and 35.0 g (1.5 mol) of lithium amide to stand in air under the conditions of 23° C. and 50% RH for 1 min, they were charged into a flask of the same type as used in Example 1, and the contents of the flask were heated to 100° C. in a nitrogen flow while stirring. Then, 312.6 g (3.0 mol) of styrene were added dropwise to the flask over 6 h while maintaining a temperature of the reaction mixture at 100° C. After completion of the dropwise addition, the resulting reaction solution was held at 100° C. for 120 min. Thereafter, 270.0 g (15.0 mol) of water corresponding to a molar amount 10 times that of the lithium amide charged were added to the reaction solution and then stirred. At this time, occurrence of odor was recognized owing to ammonia produced by the reaction between the lithium amide and water. After precipitates in the flask were removed by filtration, the resulting reaction solution was subjected to distillation under reduced pressure to remove water therefrom, thereby obtaining 1051.5 g of an amino compound X. The amount of styrene remaining unreacted was 39.8% by mass. When mixing 10 parts by mass of the amino compound X with 100 parts by mass of methanol, white precipitates were produced. Therefore, it was confirmed that polymers of styrene were by-produced.

As described above, in Comparative Examples 1 to 12 in which lithium amide was used as the catalyst, occurrence of odor was recognized, whereas in Examples 1 to 12 in which the alkali metal hydride compound was used, no odor was generated. In addition, as compared to Examples 2 to 12, in Comparative Examples 2 to 12, a large amount of the styrene remained unreacted. The reason therefor is that lithium amide as the catalyst was rapidly reacted with water in air and converted into lithium hydroxide having no catalytic activity.

INDUSTRIAL APPLICABILITY

In the process for producing an amino compound according to the present invention, it is possible to supply the amino compound in a stable manner without occurrence of odor. Therefore, the production process of the present invention requires no facility for preventing occurrence of odor and is therefore useful from the industrial viewpoints.

The invention claimed is:

1. A process for producing an amino compound, the process comprising reacting a polyamine with an alkenyl compound by an addition reaction in the presence of an alkali metal hydride compound as a sole catalyst in the process, wherein:
in the amino compound, at least one amine nitrogen of the polyamine forms an N—C bond with an olefinic carbon of the alkenyl compound; and
the polyamine is a polyamine represented by formula (1):

$$H_2N-CH_2-A-CH_2-NH_2 \qquad (1),$$

in which A is an optionally-substituted phenylene group.

2. The process according to claim 1, comprising mixing and contacting the alkali metal hydride compound with the polyamine to obtain a mixture, and adding the alkenyl compound to the mixture.

3. The process according to claim 2, comprising adding the alkenyl compound intermittently in divided parts to the mixture.

4. The process according to claim 2, wherein:
the polyamine and the alkali metal hydride compound are allowed to stand in air in the presence of water prior to reacting the mixture with the alkenyl compound; and
the amino compound contains unreacted alkenyl compound in an amount of 1% by mass or less after the addition reaction.

5. The process according to claim 4, wherein the amino compound contains unreacted alkenyl compound in an amount of 0.3% by mass or less after the addition reaction.

6. The process according to claim 4, wherein the amino compound contains unreacted alkenyl compound in an amount of 0.2% by mass or less after the addition reaction.

7. The process according to claim 4, wherein the polyamine and the alkali metal hydride compound are allowed to stand in ambient-temperature air having a relative humidity of at least 50% prior to reacting the mixture with the alkenyl compound.

8. The process according to claim 1, wherein the alkali metal hydride compound is present in an amount of from 0.01% to 3% by mass on a basis of a total amount of the alkali metal hydride compound and the polyamine.

9. The process according to claim 1, wherein the polyamine is p-xylylenediamine or m-xylylenediamine.

10. The process according to claim 1, wherein the alkenyl compound has 2 to 10 carbon atoms.

11. The process according to claim 1, wherein the alkenyl compound is an aromatic alkenyl compound.

12. The process according to claim 11, wherein the aromatic alkenyl compound is styrene or divinyl benzene.

13. The process according to claim 1, wherein the alkali metal hydride compound is lithium hydride, sodium hydride, or potassium hydride.

14. The process according to claim 1, wherein the alkenyl compound is selected from the group consisting of ethylene, propylene, butene, pentene, hexene, heptene, octene, nonene, decene, isobutylene, 2-pentene, 3-methyl-1-butene, 2-methyl-2-butene, 2,3-dimethyl-2-butene, cyclohexene, cyclohexadiene, styrene and divinyl benzene.

* * * * *